United States Patent [19]

Dergazarian

[11] 4,329,474

[45] May 11, 1982

[54] SELECTIVE SOLVENT EXTRACTION OF SYMMETRICAL TETRACHLOROPYRIDINE

[75] Inventor: Thomas E. Dergazarian, Midland, Mich.

[73] Assignee: The Dow Chemical Company, Midland, Mich.

[21] Appl. No.: 255,592

[22] Filed: Apr. 20, 1981

[51] Int. Cl.$^3$ ............................................ C07D 213/61
[52] U.S. Cl. .................................................... 546/345
[58] Field of Search ......................................... 546/345

[56] References Cited

U.S. PATENT DOCUMENTS 3,538,100  11/1970  Smith ................................. 546/345
3,668,209   6/1972  Kyriacou ............................ 546/345
3,993,654  11/1976  Dean et al. ......................... 546/345
4,225,718   9/1980  Perettie et al. .................... 546/345

FOREIGN PATENT DOCUMENTS 539034  12/1976  U.S.S.R. ............................ 546/345

Primary Examiner—Alan L. Rotman
Attorney, Agent, or Firm—John M. Sanders

[57] ABSTRACT

Sym-tet (2,3,5,6-tetrachloropyridine) is selectively extracted from a reaction mixture comprising sym-tet, iodide ions and an aprotic solvent by contacting an extractant solvent with the reaction mixture. The extractant solvent is an alkane having at least six carbon atoms.

8 Claims, No Drawings

SELECTIVE SOLVENT EXTRACTION OF SYMMETRICAL TETRACHLOROPYRIDINE

BACKGROUND OF THE INVENTION

1. Field of the Invention

This invention pertains to a process for the selective solvent extraction of symmetrical tetrachloropyridine (sym-tet) from a mixture containing an aprotic solvent, iodide ions and symmetrical tetrachloropyridine. Symmetrical tetrachloropyridine is an important commercial product which is used extensively in the preparation of insecticides.

2. Prior Art Description

Symmetrical tetrachloropyridine is prepared through a variety of processes. In a process as taught in Russian Pat. No. 539,034, an alkali dialkyl phosphite in N,N-dimethylformamide is added to 4-iodotetrachloropyridine, to form the desired symmetrical tetrachloropyridine. The reaction is carried out at temperatures from 140° C. to 160° C.

In U.S. Pat. No. 3,538,100, symmetrical tetrachloropyridine is prepared from the reaction of 2,6-dichloropyridine and chlorine in the presence of a catalyst. Pentachloropyridine is also produced as a contaminating by-product. Sym-tet precipitates out of the reaction system as crystals.

Another method for producing symmetrical tetrachloropyridine is by the reaction of pentachloropyridine with an oxidizable metal (e.g., Zn) in the presence of an acid (e.g., aqueous HCl). According to Dean et al. in U.S. Pat. No. 3,993,654, this reduction reaction is run in an aqueous medium at a temperature of 110° C. Dean et al. teaches the use of a water immiscible solvent, such as, perchlorethylene, to extract sym-tet from an aqueous medium.

It is desirous to obtain extractant solvents that selectively extract sym-tet.

SUMMARY OF THE INVENTION

In accordance with the present invention, sym-tet is selectively extracted from a mixture comprising sym-tet, iodide ions and an aprotic solvent by contacting said mixture with an extractant which is immiscible with said iodide ions and aprotic solvent, said extractant comprising an alkane having at least six carbon atoms, and then separating the extractant therefrom. Sym-tet is then recovered from the extractant.

DETAILED DESCRIPTION OF THE INVENTION

The 4-chloro substituent in pentachloropyridine is replaced with hydrogen by reacting the pentachloropyridine with a source of iodide ions and a proton donor to form symmetrical tetrachloropyridine (2,3,5,6-tetrachloropyridine). Suitable sources of iodine ions are sodium iodide, and other solvent soluble metal iodide salts or ammonium iodide salts.

The reaction is normally conducted by blending pentachloropyridine with an iodide salt dissolved in a suitable solvent, all in the presence of a a proton source such as water and/or sodium bicarbonate. Normally an organic solvent with a small amount of water serves as the reaction solvent and also as the proton source. Polar, aprotic solvents are appropriate organic solvents; examples are dimethylacetamide, methyl ethyl ketone, acetic acid, N,N-dimethylformamide, N-formylpiperidine, N-methylpyrrolidone, sulfolane and ethyl acetoacetate.

The reaction proceeds slowly at ambient room temperature and because of this, a temperature is normally chosen in the range of from about 100° C. to about 200° C. with the preferred temperatures ranging from about 130° C. to about 160° C.

While the reaction occurs with any ratio of reactants, it is advantageous that the limits of the solvent to pentachloropyridine weight ratio are about 1 to about 20. Preferred ratios are about 2 to about 5. The mole ratio of iodide ion to pentachloropyridine is usually about 0.1 to about 4. The preferred range is about 0.2 to about 2. A suitable solvent to iodide ion mole ratio is about 2 to 7. The mole ratio of the proton source to pentachloropyridine is advantageously from about 0.5 to about 4. The preferred range is about 0.5 to about 2.

When practicing the present invention at various aforementioned temperatures, mole ratios and weight ratios, a high product yield is achievable which is usually greater than about 80 percent of theoretical, based on the amount of pentachloropyridine employed as a starting material.

The reaction mixture is heated until iodine is formed and it is advantageous to reduce the iodine back to iodide for recycle rather than recovering it as elemental iodine. A reducing agent is, therefore, normally added to the reaction mixture to reduce the iodine as it is formed. Suitable examples of reducing agents are sodium formate, sodium sulfite, formic acid and sodium thiosulfate. In a preferred method of reduction, a combination of sodium sulfite, as the reducing agent, and sodium bicarbonate, as the proton donor, are employed. Both of these compounds are added at the beginning of the reaction as solids. Another preferred method is to generate sodium formate in situ by pumping liquid formic acid into the basic reaction mixture rather than adding the sodium formate as a solid. When generating sodium formate in situ, by the addition of liquid formic acid, the formic acid and sodium carbonate function as the proton donor.

At the completion of the reaction the symmetrical tetrachloropyridine product is isolated by solvent extraction. The extraction solvent must be immiscible with the aprotic solvent-iodide ion mixture, but must also be capable of dissolving large quantities of the sym-tet while at the same time extracting little or no iodide ions, aprotic solvent or other substituents, such as, pentachloropyridine and unsymmetrical tetrachloropyridine, which may be present in the reaction mixture. Suitable extraction solvents of the present invention include alkanes having at least six carbon atoms. The alkanes may be linear, branched or cyclic. Examples of suitable extractant solvents include hexane, heptane, trimethylhexane, trimethylheptane, methylcyclohexane, octane and kerosene. Additionally, products such as Isopar C and Isopar E, proprietary formulations of the Humble Oil and Refining Company for a line of high-purity isoparaffinic materials, are also suitable extractants. After the extractant solvent and the reaction mixture are brought into intimate contact with each other the extraction solvent forms an immiscible layer with the reaction mixture. The extraction solvent layer contains the symmetrical tetrachloropyridine, while the reaction mixture layer contains other by-products and remaining reactants, i.e., pentachloropyridine, unsymmetrical tetrachloropyridine, iodide ions and aprotic solvent.

While the volumetric phase ratio of the solvent extractant to the reaction mixture can vary depending upon several factors such as, the concentration of a sodium iodide in the reaction mixture, the amount of sym-tet in the reaction mixture and the aprotic solvent employed, volumetric phase ratio of from about 1:3 to about 3:1 will generally be employed. In these ratios the extractant solvent will extract essentially all of the sym-tet from the reaction mixture within a small number of extraction stages, i.e., 4 or less. Under most circumstances, an extraction or contacting period per stage of at most ten minutes is sufficient, although the extraction time usually may be reduced to one or two minutes. The most efficient ratios can be readily determined by one skilled in the art depending on the above mentioned factors.

The extractant solvent may be contacted with the sym-tet containing reaction mixture by any of the well-known procedures employed in solvent-extractions. While continuous countercurrent methods are preferred, batch, continuous batch and batch countercurrent methods may also be used. The liquid-liquid contacting means may comprise a pulse column, a countercurrent rotating disc column and other known systems. Mixing is carried out at temperatures below the boiling point of the solvent extractant advantageously in the range of about 20° C. to about 90° C. and preferably in the range of from about 20° C. to about 40° C.

After the sym-tet has been extracted from the reaction mixture phase to the solvent extractant phase, the reaction mixture phase and the solvent extractant phase are physically separated. The sym-tet is then recovered from the solvent extractant using known methods such as distillation.

The following examples further illustrate the invention but are not to be construed as limitations on the scope of the process contemplated herein.

EXAMPLE 1

A synthetic mix comprising dimethylacetamide (DMAC), NaI and sym-tet in molar ratios of 7:2:1 respectively was mixed and heated to about 80° C., cooled and then reheated to about 80° C. to achieve homogenity before adding the extractant solvent. Equal volumes of the synthetic mix and extracting solvent were placed in a water jacketed, graduated cylindrical separatory funnel. The temperature was kept at about 70° C. while an external mechanical stirrer was used to obtain equilibrium between the phases. After reaching equilibrium the stirrer was stopped and the phases were allowed to separate. A ten (10) milliliter (ml) sample of each phase was analyzed using standard gas chromatographic methods to determine the selective extractant properties of the extractant solvents. Four extractant solvents employed in the above procedure were octane, methylcyclohexane, ISOPAR® C and ISOPAR® E. The results are listed in the following Table I.

TABLE I

| Reaction Mixture | Extract (weight percent) | Synthetic Mix (weight percent) |
|---|---|---|
| *Octane | 81.64% | 0.34% |
| **DMAC | 3.61 | 64.78 |
| NaI | 1.48 | 31.36 |
| Sym-tet | 13.27 | 3.52 |
| *methylcyclohexane | 81.96% | 1.52% |
| **DMAC | 4.46 | 63.23 |
| NaI | 0.24 | 32.84 |
| Sym-tet | 13.35 | 2.41 |
| *ISOPAR® C | 81.72% | 0.56% |

TABLE I-continued

| Reaction Mixture | Extract (weight percent) | Synthetic Mix (weight percent) |
|---|---|---|
| **DMAC | 4.16 | 62.75 |
| NaI | 0.01 | 31.95 |
| Sym-tet | 14.11 | 4.73 |
| *ISOPAR® E | 82.54% | 0.44% |
| **DMAC | 4.03 | 62.92 |
| NaI | 0.03 | 32.62 |
| Sym-tet | 13.40 | 4.02 |

*denotes EXTRACTANT
**denotes aprotic solvent

EXAMPLE 2

A synthetic mix comprising DMAC, NaI and sym-tet in molar ratios of 7:1.46:1.46 respectively was mixed and heated to about 80° C., cooled and then reheated to about 80° C. to achieve homogenity before adding the extractant solvent. Equal volumes of extractant solvent and synthetic mix were placed in a water-jacketed, graduated cyclindrical separatory funnel. The temperature was kept at about 70° C. while an external mechanical stirrer was used to obtain equilibrium between the phases. After reaching equilibrium the stirrer was stopped and the phases were allowed to separate. A ten (10) ml sample of each phase was analyzed using standard gas chromatography to determine the selective extractant properties of the extractant solvents. Two (2) extractant solvents employed in the above procedure were cyclohexane and heptane. Comparisons were made of the contents (in weight percent) of the extractant and the corresponding synthetic mix. Results are in Table II.

TABLE II

| | Composition in Weight Percent | |
|---|---|---|
| | Extract | Synthetic Mix |
| *Cyclohexane | 74.5% | 3.5% |
| DMAC | 7.25 | 65.1 |
| NaI | 1.2 | 25.7 |
| Sym-tet | 17.3 | 5.56 |
| *Heptane | 73.2% | 2.91% |
| DMAC | 7.29 | 64.08 |
| NaI | 0.76 | 26.4 |
| Sym-tet | 18.7 | 6.59 |

*denotes extractant

What is claimed is:

1. A method of selectively extracting symmetrical tetrachloropyridine from a mixture comprising symmetrical tetrachloropyridine, iodide ions and an aprotic solvent, said method comprising:
   (a) contacting said mixture with an extractant which is immiscible with said iodide ions and aprotic solvent, said extractant comprising an alkane having at least six carbon atoms.

2. The method of claim 1 further comprising the step of separating said extractant from said mixture.

3. The method of claim 2 further comprising the step of recovering said symmetrical tetrachloropyridine from said extractant.

4. The method of claim 1 wherein said aprotic solvent is dimethylacetamide.

5. The method of claim 1 wherein said extractant is methylcyclohexane, trimethylhexane, cyclohexane, heptane, kerosene, octane, trimethylheptane, or mixtures thereof.

6. The method of claim 5 wherein said aprotic solvent is dimethylacetamide.

7. The method of claim 1 wherein said aprotic solvent is ethyl acetoacetate.

8. The method of claim 1 wherein said extraction is a cross-current batch extraction.

* * * * *